US007091248B2

(12) United States Patent
Brandt

(10) Patent No.: US 7,091,248 B2
(45) Date of Patent: Aug. 15, 2006

(54) TREATMENT OF ADRENOCORTICAL HYPERSECRETION AND TUMOR GROWTH

(76) Inventor: Ingvar Brandt, 756 52, Uppsala (SE)

( * ) Notice: Subject to any disclaimer, the term of this patent is extended or adjusted under 35 U.S.C. 154(b) by 38 days.

(21) Appl. No.: 10/482,203

(22) PCT Filed: Jun. 27, 2002

(86) PCT No.: PCT/SE02/01293

§ 371 (c)(1),
(2), (4) Date: Jun. 21, 2004

(87) PCT Pub. No.: WO03/002495

PCT Pub. Date: Jan. 9, 2003

(65) Prior Publication Data

US 2004/0242705 A1 Dec. 2, 2004

(30) Foreign Application Priority Data

Jun. 27, 2001 (SE) ................... 0102320

(51) Int. Cl.
A61K 31/03 (2006.01)

(52) U.S. Cl. .................................... 514/748
(58) Field of Classification Search ................ 514/748
See application file for complete search history.

(56) References Cited

OTHER PUBLICATIONS

Lund et al., Novel Involvement of a Mitochondrial Steroid Hydroxylase (P450c11) in Xenobiotic Metabolism, J. Biol. Chem. 1995 270: 20895-20897.*
Orjan Lindhe et al.: "Irreversible Binding and Adrenocorticolytic Activity of the DDT Metabolite 3-Methylsulfonyl-DDE Examined in Tissue-Slice Culture", Environmental Health Perspectives, vol. 109, No. 2, Feb. 2001, pp. 105-110.
C. Johan Jonsson et al.: "Adrenocortical Toxicity of 3-Methylsulphonyl-DDE; 3: Studies in Fetal and Suckling Mice", Reproductive Toxicology, vol. 6, No. 3, 1992, pp. 233-240.
C.J. Jonsson et al.: "Adrenocortical Toxicity of 3-Methylsulfonyl-DDE in Mice", Fundamental and Applied Toxicology, vol. 16, 1991, pp. 365-374.
Cecilia Weistrand et al.: "Methylsulfonyl metabolites of PCBs and DDE in human tissues", STN International, File CAPLUS, CAPLUS accession No. 1997:601115, Document No. 127:273940, Environ. Health Perspect. (1997), 105(6), 644-649.
Ya. G. Bal'on et al.: Synthesis of nitro- and amino-derivatives of 1,1,1-trichloro-2-(2'-chlorophyenyl)-2-(4'-chlorophenyl)ethane (2,4-DDT) and 1,1-dichloro-2-(2'-chlorophenyl)-2-(4'-chlorophenyl)ethane (2,4'-DDD), STN International, File CAPLUS, CAPLUS accession No. 1992:235159, Document No. 116:235159, Ukr. Khim. Zh. (Russ. Ed.) (1991), 57(8), 886-8.

Koichi Haraguchi et al.: "PCB methyl sulphone. Comparison of tissue levels in baltic grey seals and a Yusho patient", STN International, File CAPLUS, CAPLUS accession No. 1991:600483, Document No. 115:200483, Fukuoka Igaku Zasshi (1991), 82(5), 269-73.
A. William McBlain et al.: "Resolution of the optical isomers of o,p'-DDT", STN International, File CA, Chemical abstracts, accession No. 84:89720, Tetrahedron Lett. (1975), (49), 4351-2.
Wooten et al., "Adrenal Cortical Carcinoma, Epidemiology and Treatment with Mitotane and a Review of the Literature", CANCER, Dec. 1, 1993, vol. 72, No. 11, pp. 3145-3155.
Jonsson et al., "In vitro bioactivation of the environmental pollutant 3-methylsulphonyl-2,2-bis(4-chlorophenyl)-1,1-dichloroethene in the human adrenal gland", Toxicology Letters 71, 1994, pp. 169-175.
Johansson et al., "Effects of 3-MeSO$_2$-DDE and some CYP inhibitors on glucocorticoid steroidogenesis in the H295R human adrenocortical carcinoma cell line", Toxicology in Vitro 16, 2002, pp. 113-121.

* cited by examiner

Primary Examiner—Johann Richter
Assistant Examiner—Chukwuma Nwaonicha
(74) Attorney, Agent, or Firm—Young & Thompson

(57) ABSTRACT

Chemical substances having selective adrenal toxicity for use in medicine, especially for treatment of adrenocortical hypersecretion and tumour growth. There is provided a compound having the following formula for use in medicine, especially human medicine wherein
the first phenyl ring comprises one or more substituents $R_1$ which is halogen (F, Cl, Br or I), preferably in position 4;
$R_2$ and $R_3$ are halogen,
A is a single or double bond between the side chain carbon atoms;
the second phenyl ring comprises an electrophilic group $R_4$, preferably in position 3, which is $SO_2 R_5$ or its metabolic precursors S $R_5$ and $SOR_5$, $NO_2$ or $CF_3$, where $R_5$ is H or a lower alkyl, especially $CH_3$;
and one or more substituents R6 which is halogen (F, Cl, Br or I), preferably in position 4

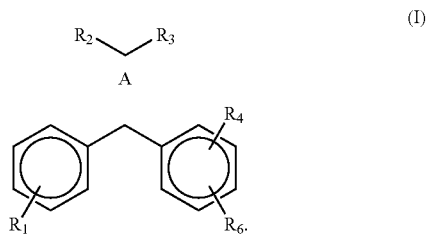

11 Claims, No Drawings

TREATMENT OF ADRENOCORTICAL HYPERSECRETION AND TUMOR GROWTH

FIELD OF THE INVENTION

The present invention relates to chemical substances having selective adrenal toxicity for use in medicine, especially for treatment of adrenocortical hypersecretion and tumour growth.

BACKGROUND OF THE INVENTION

The adrenocorticolytic activity of 1-(2-chlorophenyl)-1-(4-chlorophenyl)-2,2-dichloroethane; (o,p'-DDD, Mitotane®, Lysodren®) was first described in 1949 in dogs. Adrenal toxicity of o,p'-DDD is known to result from a cytochrome P450 (CYP)-catalysed formation of an reactive acyl chloride on the ethane side chain; this metabolite subsequently becomes irreversibly bound in the adrenal cortex, in several species including humans. The irreversible binding to vital cellular macromolecules is assumed to be of importance for the adrenal toxicity of o,p'-DDD. Metabolic activation and irreversible binding of o,p'-DDD is, however, not specific for the adrenal cortex but can occur also in other organs, such as the lung and liver. By virtue of its adrenal toxicity, o,p'-DDD is currently used as an adrenocorticolytic drug for treatment of adrenocortical carcinoma and Cushing's syndrome (1). The effective dose for treatment of adrenocortical cancer is high and gives a plasma concentration above 14 μm/ml (44 μM), whereas plasma concentrations below 10 μg/ml (31 μM) are therapeutically insufficient. Only one-third of the patients (194 out of 551) who were not cured by surgery, responded to o,p'-DDD treatment (1). In addition to hypocortisolism, o,p'-DDD gives rise to dose-dependent side effects in the gastrointestinal tract (nausea, vomiting and diarrhea) and CNS (dizziness and headaches). Treatment-related unspecific effects such as weakness and fatigue are also observed. In a substantial proportion of patients, these side effects are intolerable at therapeutic doses and the drug has to be withdrawn.

Aryl methyl sulphones of DDE and PCBs were first identified in blubber of Baltic grey seal. The sulphones form in the mercapturic acid pathway, involving sequential metabolic transformation during entero-hepatic circulation. Several of the methyl sulphones are characterized by a highly cell- and tissue-selective distribution pattern in mice. 1-(4-Chloro-3-methylsulphonylphenyl)-1-(4-chlorophenyl)-2,2-dichloroethene (MeSO$_2$-[$^{14}$C]DDE) was originally found to give rise to a cell-specific irreversible binding to cellular macromolecules in mouse adrenal zona fasciculata cells in vivo. MeSO$_2$-DDE was subsequently demonstrated to be a highly potent adrenal toxicant that induces mitochondrial degeneration and cellular necrosis following a CYP11B1-catalyzed metabolic activation in the murine adrenal cortex (2). In addition, reduced plasma corticosterone levels were observed following exposure to MeSO$_2$-DDE (3). Both the irreversible protein binding and the toxicity of MeSO2-DDE in the adrenal zona fasciculata were effectively blocked by the CYP 11B1-selective enzyme inhibitor metyrapone in mice.

SUMMARY OF THE INVENTION

In view of the many side effects of known adrenocorticolytical agents, there is a need of improved drugs for treatment of adrenocortical hypersecretion and adrenocortical tumour growth.

The present invention relates to novel treatment of adrenocortical hypersecretion. More specifically, the present invention relates to chemical substances having selective adrenal toxicity for use in medicine, especially for treatment of adrenocortical hypersecretion and tumour growth. The present invention relates in particular to MeSO$_2$-DDE and precursors thereof.

Thus, in a first aspect the present invention relates to a compound having the following formula for use in medicine, especially human medicine:

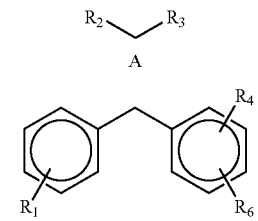

wherein
the first phenyl ring comprises one or more substituents R$_1$ which is halogen (F, Cl, Br or I), preferably in position 4. Optionally the halogen atom is radiolabelled.

In addition to the substituents R$_1$, the phenyl ring may comprise one or more substituents, e.g. lower alkyl groups, which do not affect the function of the compound in a negative way.

R$_2$ and R$_3$ which are equal or different are halogen atoms. The preferred substituent R$_2$R$_3$ being Cl$_2$, ClBr and Br$_2$.

A is a single or double bond between the side chain carbon atoms, preferably a double bond. In the case when A is a single bond, a third halogen atom may be bound to the carbon atom carrying the R$_2$R$_3$ substituents. (The tri-halogenated derivative is expected to be metabolized in vivo to the corresponding di-halogenated ethene or ethane derivative; e.g. DDE and DDD are formed by dehalogenation of DDT).

The second phenyl ring comprises an electrophilic group R$_4$, preferably in position 3, which is SO$_2$R$_5$, NO$_2$ or CF$_3$, where R$_5$ is H or a lower alkyl, especially CH$_3$. R$_4$ may also be SR$_5$ SOR$_5$, with R$_5$ as a lower alkyl, because these substituents are expected to be oxidized in vivo to SO$_2$R$_5$. (MeSO$_2$-DDEs and MeSO$_2$-PCBs are formed by sulphoxidation of the corresponding MeS and MeSO derivatives in vivo).

The second ring further comprises one or more substituents R$_6$ which is halogen (F, Cl, Br or I), preferably in position 4. Optionally the halogen atom is radiolabelled.

In addition to the substituents R$_4$ and R$_6$ the phenyl ring may comprise lower alkyl substituents which do not affect the function of the compound in a negative way.

Preferred compounds according to the invention are:
1-(4-chloro-3-methylsulphonylphenyl)-1-(4-chlorophenyl)-2,2-dichloroethene
1-(4-chloro-3-methylsulphonylphenyl)-1-(4-chlorophenyl)-2,2-dichloroethane
1-(4-chloro-3-methylsulphonylphenyl)-1-(4-chlorophenyl)-2,2-dibromoethene.

1-(4-chloro-3-methylsulphonylphenyl)-1-(4-chlorophenyl)-2,2-dichloroethene is at present the most preferred compound according to the present invention.

Further examples of compounds according to the invention include, but are not limited to:

1-(3-chloro-4-methylsulphonylphenyl)-1-(4-chlorophenyl)-2,2dichloroethene, and -2,2-dibromoethene 1-(4-bromo-3-methylsulphonylphenyl)-1-(4-bromophenyl)-2,2-dichloroethene, and -2,2-dibromoethene 1-(4-bromo-3-methylsulphonylphenyl)-1-(4-chlorophenyl)-2,2-dichloroethene, and -2,2-dibromoethene 1-(4-chloro-3-methylsulphonylphenyl)-1-(4-bromophenyl)-2,2-dichloroethene, and -2,2-dibromoethene 1-(3-bromo-4-methylsulphonylphenyl)-1-(4-bromophenyl)-2,2-dichloroethene, and -2,2-dibromoethene 1-(3-bromo-4-methylsulphonylphenyl)-1-(4-chlorophenyl)-2,2-dichloroethene, and -2,2-dibromoethene 1-(3-chloro-4-methylsulphonylphenyl)-1-(4-bromophenyl)-2,2-dichloroethene, and -2,2-dibromoethene 1-(4-chloro-3-nitrophenyl)-1-(4-chlorophenyl)-2,2-dichloroethene, and -2,2-dibromoethene 1-(3-chloro4-nitrophenyl)-1-(4-chlorophenyl)-2,2-dichloroethene, and -2,2-dibromoethene 1-(4-bromo-3-nitrophenyl)-1-(4-bromophenyl)-2,2-dichloroethene, and -2,2-dibromoethene 1-(4-bromo-3-nitrophenyl)-1-(4-chlorophenyl)-2,2-dichloroethene, and -2,2-dibromoethene 1-(4-chloro-3-nitrophenyl)-1-(4-bromophenyl)-2,2-dichloroethene, and -2,2-dibromoethene 1-(3-bromo4-nitrophenyl)-1-(4-bromophenyl)-2,2-dichloroethene, and -2,2-dibromoethene 1-(3-bromo-4-nitrophenyl)-1-(4-chlorophenyl)-2,2-dichloroethene, and -2,2-dibromoethene 1-(3-chloro-4-nitrophenyl)-1-(4-bromophenyl)-2,2-dichlorethene, and-2,2-dibromoethene 1-(4-chloro-3-trifluoromethylphenyl)-1-(4-chlorophenyl)-2,2-dichloroethene, and -2,2-dibromoethene 1-(3-chloro-4-trifluoromethylphenyl)-1-(4-chlorophenyl)-2,2-dichloroethene, and -2,2-dibromoethene 1-(4-bromo-3-trifluoromethylphenyl)-1-(4-bromophenyl)-2,2-dichloroethene, and -2,2-dibromoethene 1-(4-bromo-3-trifluoromethylphenyl)-1-(4-chlorophenyl)-2,2-dichloroethene, and -2,2-dibromoethene 1-(4-chloro-3-trifluoromethylphenyl)-1-(4-bromophenyl)-2,2-dichloroethene, and -2,2-dibromoethene 1-(3-bromo-4-trifluormethylphenyl)-1-(4-bromophenyl)-2,2-dichloroethene, and -2,2-dibromoethene 1-(3-bromo-4-trifluormethylphenyl)-1-(4-chlorophenyl)-2,2-dichloroethene, and -2,2-dibromoethene 1-(3-chloro-4-trifluoromethylphenyl)-1-(4-bromophenyl)-2,2-dichlorethene, and -2,2-dibromoethene In a second aspect, the present invention relates to a drug composition comprising one or more of the compounds according to the present invention. The composition may further comprise one or more of pharmaceutically acceptable carriers.

In a third aspect, the present invention relates to use of a compound according to above for production of a drug for treatment of adrenocortical hypersecretion, alternatively for treatment of adrenocortical tumour growth, for example adrenocortical carcinoma. Another example of use according to the invention is for treatment of Cushing's syndrome.

In a fourth aspect, the present invention relates to use of the drug composition according to the present invention for the treatment of adrenocortical hypersecretion, alternatively for treatment of adrenocortical tumour growth, for example adrenocortical carcinoma. Another example of use according to the invention is for treatment of Cushing's syndrome.

In a fifth aspect, the present invention relates to a method of treatment of adrenocortical hypersecretion, adrenocortical tumour growth, adrenocortical carcinoma or Cushing's syndrome, comprising administration of a pharmaceutically effective amount of a composition according to the present invention to a subject in need thereof.

In a sixth aspect the present invention relates to use of a compound according to the invention for diagnosing adrenocortical disorders wherein $R_4$ is $SO_2R_5$ or $CF_3$, in which $R_5$ is lower alkyl and the C-atom is a radioactive isotope (e.g. $^{11}C$). Alternatively, the $CF_3$ group contains $^{18}F$. Other halogen substituents could be $^{18}F$ or $^{76}Br$. This aspect includes application of imaging techniques such as positron emission tomography (PET).

In a seventh aspect, the present invention relates to a compound that may be labelled with a radioactive isotope for radiotherapy of adrenocortical tumours such as adrenocortical carcinoma.

DETAILED DESCRIPTION OF THE INVENTION

Materials and Methods

Normal adrenal tissue, cortex as well as apparently unaffected medulla, was obtained from a 34-year-old female MEN 2 patient operated on for an ipsilateral pheochromocytoma. Another normal adrenal was obtained from a patient operated on for a renal carcinoma.

Tissue from a lymphnode metastasis of an aldosterone producing adrenocortical carcinoma was obtained from a 54year-old male.

Tissue from a bilateral non-functioning adrenocortical hyperplasia was obtained from a 58-year-old female.

Chemicals 1-(4-Chloro-3-methylsulphonylphenyl)-1-(4-chloro-[$^{14}C$]phenyl)-2,2-dichloroethene (MeSO$_2$-[$^{14}C$]DDE; 13.4 mCi/mmol), unlabelled MeSO$_2$-DDE and 1-(2-chlorophenyl)-1-(4-chloro -[$^{14}C$]phenyl)-2,2-dichloroethane (o,p'-[$^{14}C$]DDD; 11.2 mCi/mmol) were kindly prepared by Professor Åke Bergman, Dept environmental chemistry, Stockholm University. As determined by gas chromatography mass spectroscopy, radiochemical purity values were >99%. Tetracosactide (Synacten Depot®, 1 mg/ml) was obtained from Ciba (V. Frölunda, Sweden), dimethylsulfoxide (DMSO) and agarose (Type VII, low melting temperature) were from Sigma (St. Louis, Mo.). Methacrylate Technovit 7100 was obtained from Kulzer (Wehrheim, Germany). All liquids and dyes were from Merck (Darmstadt) except chloroform, which came from Prolabo (Paris, France). Liquid film NTB 2 was purchased from Kodak (Rochester, USA).

Preparation and Incubation of Tissue Slices

Adrenal tissue was placed in ice-cold isotonic saline solution after removal and kept on ice until embedded in 3% agarose. Precision-cut slices (200 μm) were prepared in a Krumdieck tissue slicer (Alabama Research and Development, Munford, Ala., USA) in ice-cold PBS. Slices of roughly equal size were placed in culture medium on a titanium screen holder and incubated for 24 h (after a 1 h pre-incubation).

To inhibit CYP-dependent enzyme activity in the slices, incubation wells were supplemented with the CYP11B1 (11β-hydroxylase) inhibitor metyrapone (50 μM) when applicable. To stimulate ACTH-regulated enzyme activity in the slices, the synthetic ACTH-analogue tetracosactide (11 nM) was added. The labeled and unlabeled test substances (MeSO$_2$-DDE and o,p'-DDD) were added to the fresh incubation medium, dissolved in DMSO (not exceeding 0.5% of the total volume). Control slices were cultured in medium containing DMSO only.

Autoradiography

Microautoradiography: Slices were incubated with $MeSO_2$-[$^{14}C$]DDE (2.6 µM, 35 nCi/ml) or o,p'-[$^{14}C$]DDD (3.8 µM, 60 nCi/ml) for 24 h. The labeled substances were added to the medium dissolved in DMSO. Following incubation, slices were fixed overnight in buffered formaldehyde (4%). The fixed slices were dehydrated, embedded in methacrylate, sectioned, and dipped in liquid NTB2 film emulsion, as described elsewhere (4). Autoradiograms were exposed (4° C.) for one year to enable localization of irreversible binding in metyrapone-treated slices. Autoradiograms were developed, stained, and examined as previously described (4).

Phosphorautoradiography: Semi-quantification of tissue-bound radioactivity was accomplished by apposing tissue sections to imaging plates (BAS-IP MP 2040S Fuji, Japan) for 49 days. The radioactivity in the labeled areas of the adrenal sections was recorded by reading the imaging plate in a Phosphoimager (BAS 1500, Fuji, Japan). For semi-quantification of the tissue-bound radioactivity, a Windows-based bio-imaging analyzer program (ImageGauge, version 3.122, Fujifilm, Japan) was used.

In order to correlate tissue-bound radioactivity and metabolically active regions in the incubated slices, the labeled areas of the images were marked selectively at 1 pixel resolution (1 pixel=100 µm). Values obtained were expressed as PhosphoStimulated Luminescence (PSL) minus background (BG) per $mm^2$ of 2 µm thick tissue sections ((PSL-BG)/$mm^2$). The values were adjusted according to the difference in specific activity of the two compounds.

In order to check the imaging plates with respect to exposure linearity, the same plate was repeatedly exposed to the same sections for 7, 14, 28, 49 and 122 days, reading and erasing the plate between each exposure. To examine inter-exposure variation, the imaging plate was exposed repeatedly (3 times) for 7 days, reading and erasing the plate between each exposure. Intra-exposure variation was measured on three adjacent sections on the same glass-slide.

Hormone Analysis

Cortisol, 11-deoxycortisol, corticosterone, 11-deoxycorticosterone, aldosterone, androstenedione and 17-OH-progesterone concentrations in the medium were measured with HPLC using UV detection (241 nm), as described previously (4). The steroid products were separated using a linear gradient of 18–80% acetonitrile (1 ml/min), obtained by diluting acetonitrile/tetrahydrofuran (90/10 vol %) with methanol/water (40/60 vol %), for 32 min. The amounts of steroids were expressed as nmol/slice. The detection level of cortisol/corticosterone was 5 pmol/ml medium. To adjust for differences in slice size, the steroids were expressed as a percentage of the amount of cortisol from the same slice.

Statistical Evaluation of Data

Statistical analysis performed using One-way ANOVA (Bonferroni's Multiple Comparison Test as the post-test) to analyze hormone concentrations, student's t-test to analyze bound radioactivity and linear regression test to analyze exposure linearity. Significance was assigned a value of $P<0.05$. All tests were performed with GraphPad Prism software version 3.0 for Windows, GraphPad Software, San Diego, Calif., USA.

Results

Autoradiography

As determined by light microscopy, autoradiograms of normal adrenal slices exposed to $MeSO_2$-[$^{14}C$]DDE or to o,p'-[$^{14}C$]DDD showed a high and selective labeling of *zona fasciculata* and *zona reticularis*. The labeling of *zona reticularis* was markedly stronger than that of *zona fasciculata*. *Zona glomerulosa* and the adrenal medulla were devoid of bound radioactivity exceeding that of the background level.

As determined by phosphorautoradiography, no significant difference in the amount of tissue-bound radioactivity between $MeSO_2$-[$^{14}C$]DDE- and o,p'-[$^{14}C$]DDD-exposed slices could be detected. The images of tissue-bound radioactivity semi-quantified with phosphorautoradiography closely matched the images of the microautoradiograms. In slices exposed to metyrapone and $MeSO_2$-[$^{14}C$]DDE, binding in *zona fasciculata/reticularis* was inhibited below the detection limit at 49 days of exposure. In metyrapone-exposed slices, irreversible o,p'-[$^{14}C$]DDD binding in *zona fasciculata/reticularis* was inhibited by 32%, as compared with slices exposed only to o,p'-[$^{14}C$]DDD.

Slices from a lymphnode metastasis of an aldosterone producing adrenocortical carcinoma, exposed to $MeSO_2$-[$^{14}C$]DDE or to o,p'-[$^{14}C$]DDD showed a selective binding of both compounds to the adrenocortical carcinoma cells. No labeling above the background level could be observed in surrounding tissues.

In slices from a bilateral non-functioning adrenocortical hyperplasia, the levels (for both compounds) of bound radioactivity were about one-third of that in normal adrenal tissue ($P<0.001$). The binding of both compounds was inhibited to the same extent with metyrapone treatment as in the normal tissue.

Steroid Hormone Secretion

Cortisol, 11-deoxycortisol, corticosterone, 11-deoxycorticosterone, aldosterone, androstenedione and 17-OH-progesterone were all detected in the culture medium. Cortisol and corticosterone were the major secreted steroids, representing 53% and 29%, of the total steroid secretion from non-exposed control slices). In $MeSO_2$-DDE- or o,p'-DDD-exposed (25 µM) slices, no significant difference in cortisol or corticosterone secretion could be observed, compared with control slices. No difference could be observed between $MeSO_2$-DDE- or o,p'-DDD-exposed slices. A significant increase in 11-deoxycorticosterone secretion to the medium was observed in $MeSO_2$-DDE exposed slices, compared with o,p'-DDD exposed slices and control slices. Androstenedione secretion was also increased in $MeSO_2$-DDE-exposed slices, compared with o,p'-DDD-exposed slices. 11-deoxycortisol was detectable only in the culture medium of $MeSO_2$-DDE-exposed slices.

DISCUSSION

A drug according to the present invention has the potential to be more effective in specifically targeting cells producing glucocorticoid in humans than o,p'-DDD, resulting in reduced dose levels and subsequently lower unspecific toxicity compared with o,p'-DDD. Moreover, by using adrenal CYP 11B1 as the activating enzyme to produce irreversibly bound protein adducts, toxicity caused by other CYP enzymes in non-target organs should be avoided or significantly reduced compared with o,p'-DDD.

In an earlier work, the present inventor described a simple precision-cut tissue slice culture procedure, with which to examine $MeSO_2$-DDE-induced irreversible binding as well as functional and morphological changes in the adrenal cortex (4). Using this procedure, strong irreversible binding of $MeSO_2$-DDE was confirmed in the adrenal cortex in mice, whereas very weak binding occurred in rats. For a comparison, o,p'-DDD gave only a negligable irreversible binding in both mouse and rat adrenal slices, conforming with the lack of adrenocorticolytic activity of o,p'-DDD in mice and rats. Numerous chemicals are metabolically activated, irreversibly bound and toxic in the adrenal cortex in different species. To explore the possibility to develop the environmental pollutant $MeSO_2$-DDE as a drug candidate for adrenocortical hypersecretion and tumour growth, potential target cells for high irreversible binding of $MeSO_2$-DDE in normal and pathological human adrenal tissue were determined. In addition, the hitherto unknown target cells for o,p'-DDD were identified and compared with those found for $MeSO_2$-DDE.

In the present invention the slice culture procedure was consequently used to investigate CYP-catalyzed irreversible binding of $MeSO_2$-[$^{14}C$]DDE and o,p'-[$^{14}C$]DDD in cells from human tissue producing glucocorticoid ex vivo. As a result of this, the present inventor found that $MeSO_2$-DDE should have potential to be used as a drug candidate against adrenocortical disorders.

Previously reported findings in mouse adrenal tissue exposed to $MeSO_2$-[$^{14}C$]DDE ex vivo showed that strong irreversible binding was confined to *zona fasciculata*. In contrast, o,p'-[$^{14}C$]DDD binding was very weak compared with that of $MeSO_2$-[$^{14}C$]DDE.

In the present invention strong $MeSO_2$-[$^{14}C$]DDE-derived binding in human adrenal tissue was found that was confined to both *zona fasciculata* and *zona reticularis*. Irreversible o,p'-[$^{14}C$]DDD-binding was found to be localized in a similar way. Even though $MeSO_2$-[$^{14}C$]DDE concentration in the medium was almost half that of o,p'-[$^{14}C$]DDD, the levels of binding were of roughly equal strength. In mouse, the $MeSO_2$-DDE-activating enzyme CYP11B1 has been reported to be expressed only in *zona fasciculata*, whereas in human adrenal cortex, CYP11B1 is expressed in both *zona fasciculata* and *zona reticularis*, but not in *zona glomerulosa*, the adrenal medulla, or the capsule.

Metyrapone is a potent CYP11B1 inhibitor that blocks synthesis of cortisol from 11-deoxycortisol (86%, 5 µM) in V79 hamster cells transfected with human CYP11B1 DNA. It was recently reported that metyrapone inhibits irreversible $MeSO_2$-[$^{14}C$]DDE-binding and corticosterone secretion in mouse adrenal slice culture and mouse adrenal homogenate (4). Exposure of cultured human adrenal slices to metyrapone (50 µM) reduced irreversible $MeSO_2$-[$^{14}C$] DDE-binding below the detection limit, whereas o,p'-[$^{14}C$] DDD-binding was reduced only by 32%. This finding supports that $MeSO_2$-[$^{14}C$]DDE was activated by human CYP 11B1, whereas o,p'-DDD was activated by another CYP enzyme less sensitive to metyrapone (presumably CYP 11A1).

Phosphorautoradiography proved to be a quick and sensitive way to quantify levels of metabolite binding in the human adrenal cortex. Combined with the exact localization of binding obtained by microautoradiography, phosphorautoradiography is an efficient means to semi-quantify the levels of bound $MeSO_2$-[$^{14}C$]DDE- and o,p'-[$^{14}C$]DDD-adducts in the target cells (4). The linear increase in PSL/$mm^2$ values during long exposure times and low exposure-to-exposure variation favor the quantitative use of phosphorautoradiography.

In the present invention, the concentration of o,p'-DDD examined (25 µM) did not produce any visible effect on steroid secretion, compared with control. Interestingly, at the same concentration and below the therapeutically effective o,p'-DDD plasma concentration $MeSO_2$-DDE (25 µM) gave rise to an increased accumulation of 11-deoxycorticosterone, 11-deoxycortisol and androstenedione in the culture medium. In support of this finding, $MeSO_2$-DDE (10 µM) has subsequently been demonstrated to inhibit CYP 11B1 enzyme activity also in the H295R human adrenocortical carcinoma cell line (5). In homogenate incubations of cells from the human adrenal cortex, the apparent $K_m$-value of $MeSO_2$-DDE was 17 times lower than that of o,p'-DDD (1.4 and 24 µM respectively) (6). This indicates that $MeSO_2$-DDE could be toxic at lower doses than o,p'-DDD. Combined with the zone-specific irreversible binding observed, these data from the inventor's laboratory support the contention that $MeSO_2$-DDE, unlike o,p'-DDD, is a tissue-specific toxicant in the human adrenal *zona fasciculata/reticularis*. The results further show that $MeSO_2$-DDE is irreversibly bound in cells of a lymphnode metastasis of an aldosterone producing adrenocortical carcinoma, and in a nonfunctional adrenocortical hyperplasia. Also this binding was inhibited by metyrapone, supporting a CYP 11B1-catalysed metabolic activation of $MeSO_2$-DDE also in pathologically altered tissue.

Considering the low potency and the potentially severe side effects frequently observed following o,p'-DDD treatment, $MeSO_2$-DDE and its analogs should have potential as an alternative in the therapy of adrenocortical hypersecretion and tumor growth. $MeSO_2$-DDE should have potential for a higher therapeutic potency than o,p'-DDD, resulting in lower therapeutic doses than required for o,p'-DDD. The risk for unspecific side-effects should therefore be lower than for o,p'-DDD. Based on a novel activation mechanism using mitochondrial CYP 11B1, an enzyme specific for cells producing corticosteroid, $MeSO_2$-DDE should also have potential for a more targeted and selective effect in normal and cancerous adrenocortical tissue than is the case with o,p'-DDD. Side-effects resulting from CYP-catalysed irreversible binding in non-adrenal tissues should therefore be expected to be lower than when using o,p'-DDD. $MeSO_2$-DDE and its analogs presented in this invention, should provide a basis to develop an effective and safe pro-drug, lacking severe side-effects characteristic for o,p'-DDD.

REFERENCES

1. Wooten M D, King D K 1993 Adrenal cortical carcinoma: Epidemiology and treatment with mitotane and a review of the literature. Cancer 72:3145-3155.
2. Jönsson C-J, Rodriguez Martinez H, Lund B O, Bergman Å, Brandt I 1991. Adrenocortical toxicity of 3-methylsulfonyl-DDE in mice. II. Mitochondrial changes following ecologically relevant doses. Fundam Appl Toxicol 16:365-74.
3. Jönsson C-J, Lund B O, Bergman Å, Brandt I 1992 Adrenocortical toxicity of 3-methylsulphonyl-DDE: 3. Studies in fetal and suckling mice. Reprod Toxicol 6:233-240.
4. Lindhe Ö, Lund B-O, Bergman Å, Brandt I 2001 Irreversible binding and adrenocorticolytic activity of the DDT metabolite 3-methylsulphonyl-DDE examined in tissue slice culture. Environ Health Perspect 109:105-110.
5. Johansson M K, Sandersson J T, Lund B-O 2002 Effects of 3-MeSO2-DDE and some CYP inhibitors on glucocorticoid steriodogenesis in the human H295R adrenocortical cell line.

6. Jönsson C J, Lund B O 1994 In vitro bioactivation of the environmental pollutant 3-methylsulphonyl-2,2-bis(4-chlorophenyl)-1,1-dichloroethene in the human adrenal gland. Toxicol Lett 71:169–75.

What is claimed is:

1. A method of diagnosing adrenocortical disorders, comprising administering to a patient a compound having the following formula:

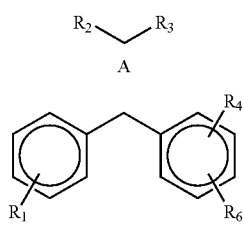

wherein the first phenyl ring comprises one or more substituents $R_1$ which is a halogen selected from the group consisting of F, Cl, Br and I;

$R_2$ and $R_3$ are each halogen atoms selected from the group consisting of F, Cl, Br and I;

A is a single or double bond between the side chain carbon atoms;

the second phenyl ring comprises an electrophilic group $R_4$, which is $SO_2R_5$ or a metabolic precursor, $SOR_5$, $NO_2$ or $CF_3$, where $R_5$ is H or a lower alkyl; and a radiolabelled substituent $R_6$ which is a halogen selected from the group consisting of F, Cl, Br and I, and diagnosing adrenocortical disorders on the basis of whether said compound is detected by imaging techniques.

2. The method according to claim 1, wherein the compound, when A is a single bond and comprises a third halogen atom bound to the carbon atom carrying the $R_2R_3$ substituents.

3. The method according to claim 1, wherein the compound is 1-(4-chloro-3-methylsulphonylphenyl)-1-(4-chlorophenyl)-2,2-dichloroethene.

4. The method according to claim 1, wherein $R_4$ in the compound is $SO_2R_5$, in which $R_5$ is lower alkyl.

5. The method according to claim 1, wherein $R_1$ is a halogen at position 4.

6. The method according to claim 1, wherein the $R_4$ group is in position 3.

7. The method according to claim 1, wherein $R_6$ is a halogen in position 6.

8. The method according to claim 1, wherein $R_4$ is $CF_3$ wherein the C-atom is $^{11}C$.

9. The method according to claim 8, wherein the $CF_3$ group contains $^{18}F$.

10. The method according to claim 8, wherein the $CF_3$ group contains $^{76}Br$.

11. The method according to claim 8, wherein the $CF_3$ group contains other halogen substituents selected from the group consisting of $^{18}F$ or $^{76}Br$.

* * * * *